United States Patent [19]

Onishi

[11] Patent Number: 4,808,709
[45] Date of Patent: Feb. 28, 1989

[54] MATRIX POLYMER AND ITS PREPARATION

[76] Inventor: Yasuhiko Onishi, 39-4, Kosora-cho, Seto-shi, Aichi-ken, Japan

[21] Appl. No.: 895,925

[22] Filed: Aug. 13, 1986

[51] Int. Cl.[4] .......................... C07G 7/00; C08B 37/02; G02C 7/04; C08F 16/38
[52] U.S. Cl. ............................... 536/112; 351/160 R; 351/160 H; 523/106; 523/108; 527/313; 527/314
[58] Field of Search ..................... 536/112; 351/160 R, 351/160 H; 527/313, 314; 523/106, 108

[56] References Cited

U.S. PATENT DOCUMENTS

| | | | |
|---|---|---|---|
| 4,264,155 | 4/1981 | Miyata | 351/160 H |
| 4,451,629 | 5/1984 | Tanaka et al. | 527/313 |
| 4,495,313 | 1/1985 | Larsen | 523/108 |
| 4,529,747 | 7/1985 | Kato et al. | 523/108 |
| 4,532,267 | 7/1985 | Allan | 351/160 H |
| 4,536,554 | 8/1985 | Lim et al. | 351/160 H |
| 4,547,543 | 10/1985 | Shibata et al. | 523/108 |

OTHER PUBLICATIONS

Bamford et al., *Polymer*, vol. 9, pp. 595–598 (1968).
J. Ferguson et al., *European Polymer Journal*, vol. 4, pp. 611–619 (1968).

*Primary Examiner*—Ronald W. Griffin
*Attorney, Agent, or Firm*—Spencer & Frank

[57] ABSTRACT

A cationic dextran compound matrix-copolymer obtained by reacting with a polymerizable unsaturated acid or a polymerizable unsaturated acid and olefin compound a dextran derivative which is introduced cationic radicals thereinto. It is highly hydrophilic and a material having a high affinity for a living body and which is, therefore, useful for making contact lenses, intraocular lenses, artificial bones and blood vessels, etc.

18 Claims, 1 Drawing Sheet

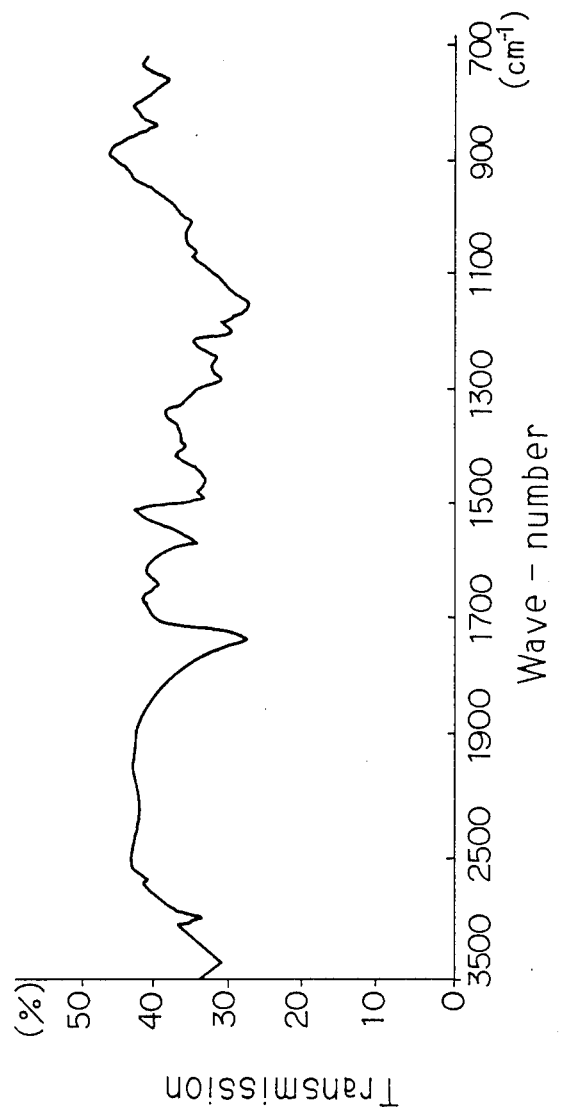

MATRIX POLYMER AND ITS PREPARATION

BACKGROUND OF THE INVENTION

This invention relates to a novel matrix-copolymer which obtained by the reaction of an unsaturated acid to dextran derivative and also to a novel matrix copolymer which obtained by the reaction of an olefinic compound to them.

The term "dextran" as herein used refers to linear polysaccharides, which is produced by fermentation of sucrose with Lactobacillaceae, having $\alpha(1-6)$ glycoside bonds and containing glucose as a recurring unit. It easily dissolves in water and is used as plasma expander, because of having a good affinities to a living body for its a stable and a gradual decomposition properties in vitro.

Matrix polymerization which suggested by Kargin et al. is carried out in existence of matrix polymer interacted with a reactive monomer or its progress chains by their hydrogen bond, Coulomb's force, charge-transfer force, and van der Waals' force. The resulting matrix-copolymer is compose of matrix polymer and the polymerized substance onto the matrix, as a polymer complex. Such a polymer complex is a useful material for a filtration membrane and a bio-material.

The inventor of this invention has succeeded in developing a novel matrix-copolymer which is composed of a dextran cationic derivative and the polymerized unsaturated acid and olefinic compound onto it, and he has found that the resulting cationic dextran matrix-copolymer is very useful for a bio-material, especially contact or intraocular lenses.

SUMMARY OF INVENTION

The matrix copolymer of this invention is obtained by reacting with a polymerizable unsaturated acid or a polymerizable unsaturated acid and olefin compound a dextran derivative which is introduced cationic radical.

If a olefin monomer having various kinds of functional groups is used and a suitable ratio of the unsaturated acid and the olefin compound to a dextran cationic derivative is chosen, it is possible to obtain a functional high polymer having a variety of functions. The matrix copolymer of this invention is highly hydrophilic, as it has a skelton of dextran. It is, therefore, a useful material having a high affinity for a living body and can, for example, be advantageously used for dental application or for making contact or Intraocular lenses or artificial bones or blood vessels or kidney.

BRIEF DESCRIPTION OF THE DRAWING

FIG. 1 is a diagram showing the infrared absorption spectra of the dextran matrix copolymer according to EXAMPLE 2 of this invention.

DESCRIPTION OF THE PREFERRED EMBODIMENT

The dextran cationic derivative which is used here is comprised of a unit derived from dextran, of the following formula (1)

$$[C_6H_7O_2(OH)_{3-a}(OX)_a]_x \cdot H_2O \quad (1)$$

wherein X is a $-(CH_2)_nR_1$ organic radical where $R_1$ is a member of the class consisting of $-NH_2$ radical, $-N(CH_3)_2$ radical, $-N(C_2H_5)_2$ radical, $-N^+(C_2H_5)_3$ radical, $-C_6H_4.NH_2$ radical, and $-CO.C_6H_4.NH_2$ radical, $-COR_2$ radical where $R_2$ is $-CH_2.NH_2$ or $-C_6H_4.NH_2$, $-CH_2CH(OH).CH_2R_3$ radical where $R_3$ is $-NH_2$, $-N(CH_3)_2$, $-N(C_2H_5)_2$, and $-N^+(C_2H_5)_3$, n is a natural number of 1 to 3, a is a positive number having a value of $0 < a \leq 3$, and x is a natural number having a value of 5 or more.

Of the hydroxyl groups of the aforesaid formula (1), the dextran esters which are partially substituted by sulfuric ester group etc. and the dextran ethers which are partially substituted by carboxymethyl ether group, alkyl ether group, etc. can be also used as the dextran cationic derivative.

With the matrix-polymerizable unsaturated acid, the compound can be shown as the following formula (2)

$$\text{(2)}$$

wherein $R_4$ is a $C_2$-$C_{16}$ organic radical having the $>C=C<$ bond.

Specific examples of the matrix-polymerizable unsaturated acid include the acrylic acid, methacrylic acid, crotonic acid, isocrotonic acid, beta, beta-dimethylacrylic acid, angelic acid, tiglic acid, and such unsaturated acids as maleic acid, fumaric acid, citraconic acid, mesaconic acid, itaconic acid, aconitic acid, and oleic acid.

These matrix-polymerization are carried out by adding the above unsaturated acid and a initiator in the solution of dextran cationic derivative.

The reaction temperature is chosen adequately about from room temperature to 70° C. In this case, the proportion in which the formula (1) dextran cationic derivative and the formula (2) matrix-polymerizable unsaturated acid are used can be suitably chosen in accordance with the end desired. Usable as the matrix-polymerization initiator in this process are ordinary radical polymerization initiators, for example, benzoyl peroxide, azobisisobutyronitrile, etc. The matrix-copolymer resulted by this reaction are insoluble in water, alcohol or a organic solvent such, for example, as acetone, tetrahydrofuran, etc., to form a poly-ion-complex structure. For this reason, it is difficult to make a membrane or molding products of this copolymer. The inventor of this invention has found that the basic type of dextran cationic derivatives can dissolve partly or completely in the afore unsaturated acids as a result of his extensive efforts to develop a matrix-copolymer. This means that matrix bulk polymerization can be done for the solution of a dextran cationic derivative in the afore unsaturated acids by using ordinary radical initiators, for example, benzoyl peroxide, azobisisobutyronitrile, etc. The reaction temperature of preferably about a room temperature to 70° C. is used. Moreover, the mixed solution consisting of the above dextran cationic derivative unsaturated acid solution and a olefin compound have been seen to be able to copolymerize by using of a ordinary radical polymerization initiators, for example, benzoyl peroxide, azobisisobutyronitrile, etc. in an amount of about 0.1% to about 1.5% by weight based on total weight. The polymerization is carried out preferably in an atmosphere of an inert gas such as nitrogen. The reaction temperature of preferably about 20° C. to 70° C. is used. The bulk copolymer can be molded freely, and may be in various forms such as boards, rods, etc. The shaped article so obtained is cut to a suitable size and thickness and is submitted to machining operations cutting, grinding, polishing and beveling to obtain the contact lens. Moreover, the composition of this invention can be fabricated into the form of artificial organs such as intraocular lenses, artificial blood vessels, artificial bones, artificial kidneys, artificial corneas or false teeth, or components of these organs. If necessary, the polymerization product can be further annealed at about 80°C.-100° C. before machining operations.

In this case, the proportion in which the dextran cationic derivative, the unsaturated acid, and polymerizable olefin compounds are used can be suitably chosen in accordance with the end desired.

The polymerizable olefin compound is a compound which can form the recurring units shown in the parentheses in the formula (3) upon polymerization.

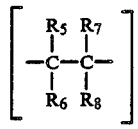  (3)

wherein $R_5$, $R_6$ and $R_7$ are each selected from the group consisting of hydrogen and $CH_3$ and $R_8$ is a member of the group consisting of

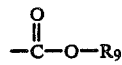

[Where $R_9$ is a member of the class consisting of hydrogen, $C_1$-$C_{12}$ alkyl radicals, cyclohexyl radical, $C_1$-$C_4$ hydroxyalkyl radicals, $C_1$-$C_8$ aminoalkyl radicals, $C_1$-$C_8$ dialkylaminoalkyl radicals, glycidyl radical, tetrahydrofuran radical, $C_1$-$C_4$ lower alkyl-substituted tetrahydrofuran radical, benzyl radical, the $(CH_2CH_2O)_yCH_2CH_2OH$ radical where y is a positive integer from 1 to 10, and $-N(R_{10})_2$ where the two $R_{10}$,s which may be the same or different, are either hydrogen or a $C_1$-$C_4$ alkyl radical];

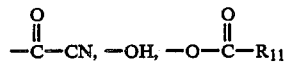

Where $R_{11}$ is a $C_1$-$C_8$ alkyl radical; phenyl radical; tolyl radical; pyridine radical; and pyrrolidone radical.

As the polymerizable olefin compound from which the unit expressed by the foregoing formula (3) is derived, there can be mentioned the alpha, beta-unsaturated acids such, for example, as acrylic acid and methacrylic acid; the alkyl esters of these alpha, beta-unsaturateds; cyclohexyl ester or lower alkyl-substituted cyclohexyl ester of the foregoing alpha, beta-unsaturated acids; the $C_1$-$C_4$ hydroxyalkyl esters of the alpha, beta-unsaturated acids such as the 2-hydroxyethyl esters, 2-hydroxypropyl ester and 2-hydroxybutyl esters of the foregoing alpha, beta-unsaturated acids; the amides or alkyl amides of the foregoing alpha, beta-unsaturated acids such as acrylamide, methacrylamide, acryl- or methacryldimethylamide; the $C_1$-$C_8$ aminoalkyl esters of the aforesaid alpha, beta-unsaturated acids; the $C_1$-$C_8$ dialkylaminoalkyl esters of the aforesaid alpha, beta-unsaturated acids; the glycidyl esters of the foregoing alpha, beta-unsaturated acids; the tetrahydrofurfuryl esters of the aforesaid alpha, beta-unsaturated acids; the benzyl esters of the foregoing alpha, beta-unsaturated acids; the polyethylene glycol monoesters such as the diethylene glycol, triethylene glycol and tetraethylene glycol monoesters of the aforesaid alpha, beta-unsaturated acids; the nitriles of the foregoing alpha, beta-unsaturated acids such as acrylonitrile and methacrylonitrile; vinyl alcohol, methylvinyl alcohol and dimethylvinyl alcohol; the $C_1$-$C_8$ alkyl esters of vinyl alcohol or the foregoing methyl-substituted vinyl alcohols such as vinyl acetate, vinyl propionate and vinyl butylate; styrene; alpha-methylstyrene and vinyl toluene; vinylpyridine; vinylpyrrolidone; and vinylmethylpyrrolidone.

EXAMPLE 1

1 g of DEAE(2-diethylaminoethyl)-dextran hydrochloride (nitrogen content 5%) derived from dextran having a weight average molecular weight of 500,000 was dissolved in 50 ml of water, 50 ml of a 0.75% aqueous solution of sodium methacrylate was more added in the solution, and then the polymerization was initiated by using 10 ml of potassium persulfate aqueous solution $(8.9 \times 10^{-3}$ mol/l). The polymerization was carried out in the sealed glass tube at 30° C. for 70 hours. After the polymerization, the reaction mixture was poured into 3-fold amount (volume) of acetone to form a precipitate. The precipitate was centrifuged and dried for 8 hours at 50° C. under reduced pressure to afford 0.96 g of the resulting matrix-copolymer having a poly-ion-complex structure. The content of nitrogen was 3.8% and the total yields(%) was 70%. This product was insoluble, in water, methanol and acetone.

EXAMPLE 2

To the aqueous solution of DEAE(2-diethylaminoethyl)-dextran hydrochloride (nitrogen content 5%) derived from dextran having a weight average molcular weight of 500,000 was added a 50% aqueous solution of sodium hydroxide above pH11 to form the precipitate of basic type DEAE-dextran. Ten grams of the so obtained basic type DEAE-dextran was dissolved in 20 ml of methacrylic acid and to the solution was added 450 ml of methyl methacrylate with stirring. Then, 2.5 g of azobisisobutyronitrile (AIBN) was added and dissolved. The solution was then transferred to a glass tube having a diameter of 15 mm and, after the tube was deaired, it was sealed and heated for 72 hours in a water bath of 50° C. and thereafter for 3 hours in an air bath of 80° C. After cooling, a rodlike product was withdrawn from the glass tube. This product was then annealed for 24 hours in an air bath of 80° C. The weight of this product was 470 g and it was insoluble in water, alcohol or a organic solvent such, for example, as acetone, tetrahydrofuran, n-hexane, etc. The Vicat softening point of this product was 93.3° C. and its Rockwell hardness (M scale) was 86. The Vicat softening point was determined in accordance with the ASTM method D1525, while the Rockwell hardness was measured in accordance with the ASTM method D 785. FIG. 1 shows the infrared absorption spectra of the resulting matrix-copolymer. The spectrum of the matrix-copolymer has some characteristic absorption band, e.g. the bands at around 2650 cm$^{-1}$(A) and at 1720 cm$^{-1}$ are attributed to $CH_3$-C stretching vibrations of DEAE-dextran and to C=O stretching vibration of poly(methacrylic acid) and poly(methyl methacrylate), respectively. On the other hand, the absorption at 1635 cm$^{-1}$ ascribable to —C=C— is seen very little in this spectrum. Further, as hereinbefore indicated, the reaction product is insoluble in the common solvents for the DEAE-dextran, poly(methacryl acid), and poly(methyl methacrylate), which have been used as starting materials, and expecially in acetone.

It is thus seen from the foregoing facts that the product obtained by the invention process is not a simple mixture but a copolymer which has a different solubility from those of starting materials.

EXAMPLE 3

The procedure of EXAMPLE 2 was repeated, except that 25 g of basic type DEAE-dextran, 50 ml of methacrylic acid, 325 ml of methyl methacrylate, and 1.8 g of AIBN were used. There were obtained 380 g of a bulk polymer in the shape of a bar. It was insoluble in water, alcohol or a organic solvent such, for example, as acetone, tetrahydrofuran, n-hexane, etc. This product had a Rockwell hardness (M scale) of 68 (ASTM D785) and a Vicat softening point of 87° C. (ASTM D1525).

EXAMPLE 4

5 g of HPTMA(2-hydroxypropyltrimethylammonium)-dextran hydrochloride (nitrogen content 3.3%) having a weight average molecular weight of 80,000 was dissolved in 100 ml of water. The above aqueous solution of HPTMA-dextran hydrochloride was adjusted above pH 11 by the use of a 50% sodium hydroxide aqueous solution and introduced into 3-fold amount (volume) of acetone to form a precipitate. The precipitate was dissolved in 20 ml of acrylic acid. By using 120 mg of AIBN, the solution was polymerized as in EXAMPLE 2 to obtain 23 g of a bulk polymer in the shape of a bar. It was insoluble in water, methyl alcohol or a organic solvent such, for example, as acetone, tetrahydrofuran, n-hexane, etc. This product had a Rockwell hardness (M scale) of 50 (ASTM D785).

EXAMPLE 5

After treated with hot water and dried, the rodlike matrix-copolymer obtained in EXAMPLE 2 was cut with a lathe rotating at 2000 rpm. At the same rotatig speed, the surface of the cut pieces was rendered concave and convex to give a predetermined curvature. The product was fitted in a pit dish on a lens polisher and polished by an upper member rotating at 15 rpm and a lower member rotating at 200 rpm. The polished product was beveled by a beveling machine to yield a contact lens. The lens had a hydrophilic surface and showed a good hydrophilicity at a contact angle of 56° as compared with a conventional poly(methyl methacrylate) lens having a contact angle of 72°.

The lens was tested with a power of −4.50 for a person whose eyes had both a sight of 0.01 (1.0×S−4.50) and who could not withstand any conventional poly(methyl methacrylate) lens. He could continue wearing the lens for eight hours. The lens gave a sight of 1.0 to both of his eyes. After he had used the lens for a year, the base curve and power of the lens were examined, but did not reveal any change. The details of the lens were as follows:

|  | Base curve | Power | Size |
| --- | --- | --- | --- |
| Left eye | 740 mm | −4.50 | 8.8 mm |
| Right eye | 745 mm | −4.50 | 8.8 mm |

EXAMPLE 6

Contact lenses were obtained by operating as in EXAMPLE 5, using the rodlike matrix-copolymer obtained in EXAMPLE 4.

A clinical test was conducted using the so obtained contact lenses with a power of −5.50. A patient whose eyes had both a sight of 0.02 (1.0×S−5.00) and who could not withstand any conventional poly(methyl methacrylate) lens could continue wearing the lens for eight hours. The lens could be worn with no trouble for a year and gave a sight of 1.0 to both of his eyes. The details of the lens were as follows:

|  | Base curve | Power | Size |
| --- | --- | --- | --- |
| Left eye | 760 mm | −5.00 | 8.8 mm |
| Right eye | 765 mm | −5.00 | 8.8 mm |

EXAMPLE 7

100 mg of matrix-copolymer of DEAE-dextran and sodium methacrylate obtained in EXAMPLE 1 was placed in a stainless steel mold. Then, the mold was pressed in a vacuum at 10 ton/cm$^2$ gauge using a hydraulic press to get its tablet. The blood clotting test was performed on the tablet in a watch glass by gravimetric measurement of the amount of clot formed at 37° C. for 8 minutes, after the addition of calcium chloride solution (0.1M, 0.01 ml) to ACD blood (0.1 ml, A type) which had been in contact with the material. The ACD blood of type A (Japan Red Cross Hospital Blood Center) was prepared by adding the blood to an anticoagulant citrate dextrose solution consisting of sodium citrate, citric acid and dextrose and kept in a thermostat at 4°–6° C. In the blood clotting test, the percentage of thrombus formed is normalized so that the comparable value (37° C., 8 minutes) for glass, which has been used as a standard material, become 100%. The results of the blood clotting test were as follows:

The percentage of thrombus formed on the glass: 100%.

The percentage of thrombus formed on the sample tablet: 70%.

It was concluded from the above results that the matrix-copolymer of DEAE-dextran and sodium methacrylate has a good thromboresistance.

What is claimed is:

1. A cationic dextran compound matrix-copolymer comprising a unit derived from a cationic dextran of the following formula (A)

$$[C_6H_7O_2(OH)_{3-a}(OX)_a]_x \cdot H_2O \quad (A)$$

wherein X is a —(CH$_2$)$_n$R$_1$ organic radical where R$_1$ is a member of the class consisting of —NH$_2$ radical, —N(CH$_3$)$_2$ radical, —N(C$_2$H$_5$)$_2$ radical, —N$^+$(C$_2$H$_5$)$_3$ radical, —C$_6$H$_4$.NH$_2$ radical, and —CO.C$_6$H$_4$.NH$_2$ radical, —COR$_2$ radical where R$_2$ is —CH$_2$.NH$_2$ or —C$_6$H$_4$.NH$_2$, —CH$_2$CH(OH).CH$_2$R$_3$ radical where R$_3$ is —NH$_2$, —N(CH$_3$)$_2$, —N(C$_2$H$_5$)$_2$, and —N$^+$(C$_2$H$_5$)$_3$, n is a natural number of 1 to 3, a is a positive number having a value of 0<a≦3, and x is a natural number having a value of 5 or more; and a unit derived from a polymerizable unsaturated acid of the following formula (B)

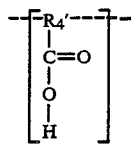

wherein R$_4'$ is a C$_2$-C$_{16}$ organic radical having the

bond derived from the >C=C< bond

2. A process for preparing a cationic dextran compound matrix-copolymer which comprises reacting a cationic dextran of the following formula (A)

[C$_6$H$_7$O$_2$(OH)$_{3-a}$.(OX)$_a$]$_x$.H$_2$O  (A)

wherein X is a —(CH$_2$)$_n$R$_1$ organic radical where R$_1$ is a member of the class consisting of —NH$_2$ radical, —N(CH$_3$)$_2$ radical, —N(C$_2$H$_5$)$_2$ radical, —N$^+$(C$_2$H$_5$)$_3$ radical, —C$_6$H$_4$.NH$_2$ radical, and —CO.C$_6$H$_4$.NH$_2$ radical, —COR$_2$ radical where R$_2$ is —CH$_2$.NH$_2$ or —C$_6$H$_4$.NH$_2$, —CH$_2$CH(OH).CH$_2$R$_3$ radical where R$_3$ is —NH$_2$, —N(CH$_3$)$_2$, —N(C$_2$H$_5$)$_2$, and —N$^+$(C$_2$H$_5$)$_3$, n is a natural number of 1 to 3, a is a positive number having a value of 0<a≦3, and x is a natural number having a value of 5 or more; with a polymerizable unsaturated acid of the following formula (B')

wherein R$_4$ is a C$_2$-C$_{16}$ organic radical having the >C=C< bond

3. A shaped article of a cationic dextran compound matrix-copolymer comprising a unit derived from a cationix dextran of the following formula (A)

[C$_6$H$_7$O$_2$(OH)$_{3-a}$.(OX)$_a$]$_x$.H$_2$O  (A)

wherein X is a —(CH$_2$)$_n$R$_1$ organic radical where R$_1$ is a member of the class consisting of —NH$_2$ radical, —N(CH$_3$)$_2$ radical, —N(C$_2$H$_5$)$_2$ radical, —N$^+$(C$_2$H$_5$)$_3$ radical, —C$_6$H$_4$. NH$_2$ radical, and —CO.C$_6$H$_4$.NH$_2$ radical, —COR$_2$ radical where R$_2$ is —CH$_2$.NH$_2$ or —C$_6$H$_4$.NH$_2$, —CH$_2$CH(OH).CH$_2$R$_3$ radical where R$_3$ is —NH$_2$, —N(CH$_3$)$_2$, —N(C$_2$H$_5$)$_2$, and —N$^+$(C$_2$H$_5$)$_3$, n is a natural number of 1 to 3, a is a positive number having a value of 0<a≦3, and x is a natural number having a value of 5 or more; and a unit derived from a polymerizable unsaturated acid of the following formula(B)

wherein R$_4'$ is a C$_2$-C$_{16}$ organic radical having the

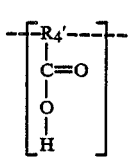

bond derived from the >C=C< bond.

4. A shaped article of claim 3 wherein said shaped article is a contact lens.

5. A process for preparing a shaped article of a cationic dextran compound matrix-copolymer which comprises reacting in a mold a cationic dextran of the following formula (A)

[C$_6$H$_7$O$_2$(OH)$_{3-a}$.(OX)$_a$]$_x$.H$_2$O  (A)

wherein X is a —(CH$_2$)$_n$R$_1$ organic radical where R$_1$ is a member of the class consisting of —NH$_2$ radical, —N(CH$_3$)$_2$ radical, —N(C$_2$H$_5$)$_2$ radical, —N$^+$(C$_2$H$_5$)$_3$ radical, —C$_6$H$_4$.NH$_2$ radical, and —CO.C$_6$H$_4$.NH$_2$ radical, —COR$_2$ radical where R$_2$ is —CH$_2$.NH$_2$ or —C$_6$H$_4$.NH$_2$, —CH$_2$CH(OH).CH$_2$R$_3$ radical where R$_3$ is —NH$_2$, —N(CH$_3$)$_2$, —N(C$_2$H$_5$)$_2$, and —N$^+$(C$_2$H$_5$)$_3$, n is a natural number of 1 to 3, a is a positive number having a value of 0<a≦3, and x is a natural number having a value of 5 or more; with a polymerizable unsaturated acid of the following formula (B')

wherein R$_4$ is a C$_2$-C$_{16}$ organic radical having the >C=C< bond

6. A cationic dextran compound matrix-copolymer comprising a unit derived from a cationic dextran of the following formula (A)

[C$_6$H$_7$O$_2$(OH)$_{3-a}$.(OX)$_a$]$_x$.H$_2$O  (A)

wherein X is a —(CH$_2$)$_n$R$_1$ organic radical where R$_1$ is a member of the class consisting of —NH$_2$ radical, —N(CH$_3$)$_2$ radical, —N(C$_2$H$_5$)$_2$ radical, —N$^+$(C$_2$H$_5$)$_3$ radical, —C$_6$H$_4$.NH$_2$ radical, and —CO.C$_6$H$_4$.NH$_2$ radical, —COR$_2$ radical where R$_2$ is —CH$_2$.NH$_2$ or —C$_6$H$_4$.NH$_2$, —CH$_2$CH(OH).CH$_2$R$_3$ radical where R$_3$ is —NH$_2$, —N(CH$_3$)$_2$, —N(C$_2$H$_5$)$_2$, and —N$^+$(C$_2$H$_5$)$_3$, n is a natural number of 1 to 3, a is a positive number having a value of 0<a≦3, and x is a natural number having a value of 5 or more; a unit derived from a polymerizable unsaturated acid of the following formula (B)

wherein R$_4'$ is a C$_2$-C$_{16}$ organic radical having the

bond derived from the >C=C< bond and a unit derived from a polymerizable olefin compound of the following formula (C)

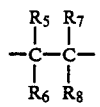  (C)

wherein $R_5$, $R_6$ and $R_7$ are each selected from the group consisting of hydrogen and $CH_3$ and $R_8$ is a member of the group consisting of

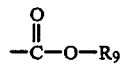

where $R_9$ is a member of the class consisting of hydrogen, $C_1$-$C_{12}$ alkyl radicals, cyclohexyl radical, $C_1$-$C_4$ hydroxyalkyl radicals, $C_1$-$C_8$ aminoalkyl radicals, $C_1$-$C_8$ dialkylaminoalkyl radicals, glycidyl radical, tetrahydrofuran radical, $C_1$-$C_4$ lower alkyl-substituted tetrahydrofuran radical, benzyl radical, the $(CH_2CH_2O)_yCH_2CH_2OH$ radical where y is a positive integer from 1 to 10, and $—N(R_{10})_2$ where the two $R_{10}$,s which may be the same or different, are either hydrogen or a $C_1$-$C_4$ alkyl radical;

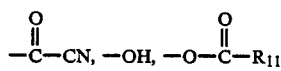

where $R_{11}$ is a $C_1$-$C_8$ alkyl radical; phenyl radical; tolyl radical; pyridine radical; and pyrrolidone radical.

7. A process for preparing a cationic dextran compound matrix-copolymer which comprises reacting a cationic dextran of the following formula (A)

$$[C_6H_7O_2(OH)_{3-a}\cdot(OX)_a]_x\cdot H_2O \qquad (A)$$

wherein X is a $—(CH_2)_nR_1$ organic radical where $R_1$ is a member of the class consisting of $—NH_2$ radical, $—N(CH_3)_2$ radical, $—N(C_2H_5)_2$ radical, $—N^+(C_2H_5)_3$ radical, $—C_6H_4.NH_2$ radical, and $—CO.C_6H_4.NH_2$ radical, $—COR_2$ radical where $R_2$ is $—CH_2.NH_2$ or $—C_6H_4.NH_2$, $—CH_2CH(OH).CH_2R_3$ radical where $R_3$ is $—NH_2$, $—N(CH_3)_2$, $—N(C_2H_5)_2$, and $—N^+(C_2H_5)_3$, n is a natural number of 1 to 3, a is a positive number having a value of $0 < a \leq 3$ and x is a natural number having a value of 5 or more; with a polymerizable unsaturated acid of the following formula (B')

$$R_4—\overset{\overset{O}{\|}}{C}—OH \qquad (B')$$

wherein $R_4$ is a $C_2$-$C_{16}$ organic radical having the >C=C< bond; and a polymerizable olefin compound of the formula (C')

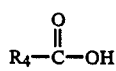  (C')

wherein $R_5$, $R_6$ and $R_7$ are each selected from the group consisting of hydrogen and $CH_3$ and $R_8$ is a member of the group consisting of

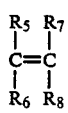

where $R_9$ is a member of the class consisting of hydrogen, $C_1$-$C_{12}$ alkyl radicals, cyclohexyl radical, $C_1$-$C_4$ hydroxyalkyl radicals, $C_1$-$C_8$ aminoalkyl radicals, $C_1$-$C_8$ dialkylaminoalkyl radicals, glycidyl radical, tetrahydrofuran radical, $C_1$-$C_4$ lower alkyl-substituted tetrahydrofuran radical, benzyl radical, the $(CH_2CH_2O)_yCH_2CH_2OH$ radical where y is a positive integer from 1 to 10, and $—N(R_{10})_2$ where the two $R_{10}$,s which may be the same or different, are either hydrogen or a $C_1$-$C_4$ alkyl radical;

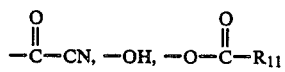

where $R_{11}$ is a $C_1$-$C_8$ alkyl radical; phenyl radical; tolyl radical; pyridine radical; and pyrrolidone radical.

8. A shaped article of a cationic dextran compound matrix-copolymer comprising a unit derived from a cationic dextran of the following formula (A)

$$[C_6H_7O_2(OH)_{3-a}\cdot(OX)_a]_x\cdot H_2O \qquad (A)$$

wherein X is a $—(CH_2)_nR_1$ organic radical where $R_1$ is a member of the class consisting of $—NH_2$ radical, $—N(CH_3)_2$ radical, $—N(C_2H_5)_2$ radical, $—N^+(C_2H_5)_3$ radical, $—C_6H_4.NH_2$ radical, and $—CO.C_6H_4.NH_2$ radical, $—COR_2$ radical where $R_2$ is $—CH_2.NH_2$ or $—C_6H_4.NH_2$, $—CH_2CH(OH).CH_2R_3$ radical where $R_3$ is $—NH_2$, $—N(CH_3)_2$, $—N(C_2H_5)_2$, and $—N^+(C_2H_5)_3$, n is a natural number of 1 to 3, a is a positive number having a value of $0 < a \leq 3$, and x is a natural number having a value of 5 or more; a unit derived from a polymerizable unsaturated acid of the following formula (B)

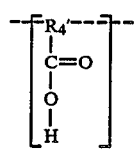  (B)

wherein $R_4'$ is a $C_2$-$C_{16}$ organic radical having the

bond derived from the >C=C< bond and a unit derived from a polymerizable olefin compound of the following formula (C)

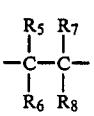  (C)

wherein $R_5$, $R_6$ and $R_7$ are each selected from the group consisting of hydrogen and $CH_3$ and $R_8$ is a member of the group consisting of

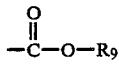

where R₉ is a member of the class consisting of hydrogen, $C_1$–$C_{12}$ alkyl radicals, cyclohexyl radical, $C_1$–$C_4$ hydroxyalkyl radicals, $C_1$–$C_8$ aminoalkyl radicals, $C_1$–$C_8$ dialkylaminoalkyl radicals, glycidyl radical, tetrahydrofuran radical, $C_1$–$C_4$ lower alkyl-substituted tetrahydrofuran radical, benzyl radical, the $(CH_2CH_2O)_yCH_2CH_2OH$ radical where y is a positive integer from 1 to 10, and —N(R₁₀)₂ where the two R₁₀s which may be the same or different, are either hydrogen or a $C_1$–$C_4$ alkyl radical;

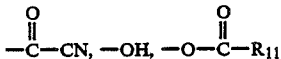

where R₁₁ is a $C_1$–$C_8$ alkyl radical; phenyl radical; tolyl radical; pyridine radical; and pyrrolidone radical.

9. A shaped article of claim 8 wherein said shaped article is a contact lens.

10. A process for preparing a shaped article of a cationic dextran compound matrix-copolymer which comprises reacting in a mold a cationic dextran of the following formula (A)

$$[C_6H_7O_2(OH)_{3-a}(OX)_a]_x \cdot H_2O \tag{A}$$

wherein X is a —(CH₂)ₙR₁ organic radical where R₁ is a member of the class consisting of —NH₂ radical, —N(CH₃)₂ radical, —N(C₂H₅)₂ radical, —N⁺(C₂H₅)₃ radical, —C₆H₄.NH₂ radical, and —C0.C₆H₄.NH₂ radical, —COR₂ radical where R₂ is —CH₂.NH₂ or —C₆H₄.NH₂, —CH₂CH(OH).CH₂R₃ radical where R₃ is —NH₂, —N(CH₃)₂, —N(C₂H₅)₂, and —N⁺(C₂H₅)₃, n is a natural number of 1 to 3, a is a positive number having a value of 0<a≦3, and x is a natural number having a value of 5 or more; with a polymerizable unsaturated acid of the following formula (B')

wherein R₄ is a $C_2$–$C_{16}$ organic radical having the >C=C< bond; and a polymerizable olefin compound of the formula (C')

wherein R₅, R₆ and R₇ are each selected from the group consisting of hydrogen and CH₃ and R₈ is a member of the group consisting of

where R₉ is a member of the class consisting of hydrogen, $C_1$–$C_{12}$ alkyl radicals, cyclohexyl radical, $C_1$–$C_4$ hydroxyalkyl radicals, $C_1$–$C_8$ aminoalkyl radicals, $C_1$–$C_8$ dialkylaminoalkyl radicals, glycidyl radical, tetrahydrofuran radical, $C_1$–$C_4$ lower alkyl-substituted tetrahydrofuran radical, benzyl radical, the $(CH_2CH_2O)_yCH_2CH_2OH$ radical where y is a positive integer from 1 to 10, and —N(R₁₀)₂ where the two R₁₀s which may be the same or different, are either hydrogen or a $C_1$–$C_4$ alkyl radical;

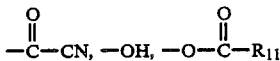

where R₁₁ is a $C_1$–$C_8$ alkyl radical; phenyl radical; tolyl radical; pyridine radical; and pyrrolidone radical.

11. The cationic dextran compound matrix-copolymer set forth in claim 1, wherein said polymerizable unsaturated acid is selected from group consisting of acrylic acid, methacrylic acid, crotin acid, isocrotonic acid, beta, betadimethylacrylic acid, angelic acid, tiglic acid, maleic acid, fumaric acid, citraconic acid, mesaconic acid, itaconic acid, aconitic acid, and oleic acid.

12. The process for preparing cationic dextran compound matrix-copolymer set forth in claim 2, wherein said polymerizable unsaturated acid is selected from the group consisting of acrylic acid, methacrylic acid, crotonic acid, isocrotonic acid, beta, beta-dimethylacrylic acid, angelic acid, tiglic acid, maleic acid, fumaric acid, citraconic acid, mesaconic acid, itaconic acid, aconitic acid, and oleic acid.

13. The shaped article of a cationic dextran compound matrix-copolymer set forth in claim 3, wherein said polymerizable unsaturated acid is selected from the group consisting of a acylic acid, methacrylic acid, matrix-polyerizable unsaturated acid include the acrylic acid, methacrylic acid, crotonic acid, isocrotonic acid, beta, beta-dimethylacrylic acid, angelic acid, tiglic acid, maleic acid, fumaric acid, citraconic acid, mesaconic acid, itaconic acid, aconitic acid, and oleic acid.

14. The process for preparing a shaped article of a cationic dextran compound matrix-copolymer set forth in claim 5, wherein said polymerizable unsaturated acid is selected from the group consisting of acrylic acid, methacrylic acid, crotonic acid, isocrotonic acid, beta, beta-dimethylacrylic acid, angelic acid, tiglic acid, maleic acid, fumaric acid, citraconic acid, mesaconic acid, itaconic acid, aconitic acid, and oleic acid.

15. The cationic dextran compound matrix-copolymer set forth in claim 6, where said polymerizable unsaturated acid is selected from the group consisting of acrylic acid, methyacrylic acid, crotonic acid, isocrotonic acid, beta, beta-dimethylacrylic acid, angelic acid, tiglic acid, maleic acid, fumaric acid, citraconic acid, mesaconic acid, itaconic acid, aconitic acid, and oleic acid.

16. The process for preparing a cationic dextran compound matrix-copolymer set forth in claim 7, wherein said polymerizable unsaturated acid is selected from the group consisting of acrylic acid, methyacrylic acid, crotonic acid, isocrotonic acid, beta, beta-dimethylacrylic acid, angelic acid, tiglic acid, maleic acid, fumaric acid, citraconic acid, mesaconic acid, itaconic acid, aconitic acid, and oleic acid.

17. The shaped article of a cationic dextran compound matrix-copolymer set forth in claim 8, wherein said polymerizable unsaturated acid is selected from the group consisting of acrylic acid, methacrylic acid, crotonic acid, isocrotonic acid, beta, beta-dimethylacrylic acid, angelic acid, tiglic acid, maleic acid, fumaric acid, citraconic acid, mesaconic acid, itaconic acid, aconitic acid, and oleic acid.

18. The process for preparing a shaped article of a cationic dextran compound matrix-copolymer set forth in claim 10 wherein said polymerizable unsaturated acid is selected from the group consisting of acrylic acid, methacrylic acid, crotonic acid, isocronitic acid, beta, beta-dimethylacrylic acid, angelic acid, tiglic acid, and such unsaturated acids as maleic acid, fumaric acid, citraconic acid, mesaconic acid, itaconic acid, aconitic acid, and oleic acid.

* * * * *